(12) United States Patent
Ludwig et al.

(10) Patent No.: US 11,478,382 B2
(45) Date of Patent: Oct. 25, 2022

(54) COMPRESSION DRESSING

(71) Applicant: KARL OTTO BRAUN GMBH & CO. KG, Wolfstein (DE)

(72) Inventors: Uwe Ludwig, Wolfstein (DE); Ferdinand Tamoue, Duelmen (DE); Marita Meister, Kaiserslautern (DE)

(73) Assignee: Karl Otto Braun GmbH & Co. KG, Wolfstein (DE)

( * ) Notice: Subject to any disclaimer, the term of this patent is extended or adjusted under 35 U.S.C. 154(b) by 260 days.

(21) Appl. No.: 16/064,706

(22) PCT Filed: Dec. 23, 2016

(86) PCT No.: PCT/EP2016/082626
§ 371 (c)(1),
(2) Date: Jun. 21, 2018

(87) PCT Pub. No.: WO2017/109209
PCT Pub. Date: Jun. 29, 2017

(65) Prior Publication Data
US 2019/0008686 A1    Jan. 10, 2019

(30) Foreign Application Priority Data
Dec. 23, 2015 (DE) .................. 10 2015 226 706.7

(51) Int. Cl.
*A61F 13/00* (2006.01)
*A61F 13/02* (2006.01)
(Continued)

(52) U.S. Cl.
CPC .. *A61F 13/00029* (2013.01); *A61F 13/00038* (2013.01); *A61F 13/0273* (2013.01);
(Continued)

(58) Field of Classification Search
CPC .......... A61F 13/00029; A61F 13/00034; A61F 13/00038; A61F 13/0273; A61F 13/08;
(Continued)

(56) References Cited

U.S. PATENT DOCUMENTS

| 4,897,297 A * | 1/1990 | Zafiroglu .................. A61F 7/02 112/420 |
| 4,998,421 A | 3/1991 | Zafiroglu |

(Continued)

FOREIGN PATENT DOCUMENTS

| DE | 19746913 A1 | 4/1999 |
| DE | 102005033720 A1 | 1/2007 |

(Continued)

OTHER PUBLICATIONS

International Search Report and Written Opinion from PCT/EP2016/082626 dated Mar. 16, 2017.
(Continued)

*Primary Examiner* — Alireza Nia
*Assistant Examiner* — Trisha Talapatra
(74) *Attorney, Agent, or Firm* — Dilworth & Barrese, LLP

(57) ABSTRACT

There is provided herein a compression dressing comprising a first cushion layer (1) and a second support layer (2) wherein the two layers (1,2) are connected to each other in the unstretched state by means of a stich-bonding process via an elastic sewing thread, the stich length being 1.5 to 3mm/U at a sewing thread tension of at most 4 cN.

19 Claims, 3 Drawing Sheets

(51) Int. Cl.
*A61F 13/06* (2006.01)
*A61F 13/08* (2006.01)
*D04B 21/16* (2006.01)

(52) U.S. Cl.
CPC ............ *A61F 13/069* (2013.01); *A61F 13/08* (2013.01); *D04B 21/165* (2013.01); *A61F 2013/00238* (2013.01); *D10B 2509/028* (2013.01)

(58) Field of Classification Search
CPC .. A61F 2013/00093; A61F 2013/00097; A61F 2013/00102; A61F 2013/00106; A61F 2013/00119; A61F 2013/00131; A61F 13/00004; A61F 13/00008; A61F 13/00021; A61F 13/069; A61F 2013/00089; A61F 2013/00238; D10B 2509/00; D10B 2509/02; D10B 2509/022; D10B 2509/028; D04B 21/165; D04B 21/18
USPC ...... 602/75–76, 60–63, 45, 53, 58; 139/421, 139/422; 112/96, 315
See application file for complete search history.

(56) References Cited

U.S. PATENT DOCUMENTS

| | | | |
|---|---|---|---|
| 6,555,730 B1 | 4/2003 | Albrod et al. | |
| 6,663,584 B2* | 12/2003 | Griesbach, III | .... A61F 13/0273 602/76 |
| 6,787,681 B2* | 9/2004 | Murakami | ............. A61L 15/24 602/54 |
| 7,886,776 B2 | 2/2011 | Jung et al. | |
| 2006/0229544 A1 | 10/2006 | Schuren et al. | |
| 2007/0178795 A1* | 8/2007 | Stralin | ................ D04H 1/4382 442/408 |
| 2009/0208698 A1 | 8/2009 | Langen | |
| 2011/0071453 A1 | 3/2011 | Schuren et al. | |
| 2012/0238933 A1* | 9/2012 | Murphy | ................ A61F 13/085 602/53 |
| 2013/0085435 A1* | 4/2013 | Murphy | ................ A61K 47/42 424/443 |
| 2013/0226062 A1* | 8/2013 | Kloeppels | ........... A61F 13/0273 602/44 |
| 2014/0052043 A1 | 2/2014 | Steinlechner et al. | |
| 2014/0121581 A1 | 5/2014 | Richardson et al. | |
| 2014/0121627 A1* | 5/2014 | Lepore | ............. A61F 13/00038 604/385.01 |
| 2014/0295190 A1* | 10/2014 | Macedo | ................. B32B 38/08 428/424.4 |
| 2015/0218742 A1 | 8/2015 | Stralin et al. | |
| 2017/0073899 A1* | 3/2017 | Wagner | .................. D21H 13/24 |
| 2018/0169963 A1* | 6/2018 | Dua | .................... B29C 66/8362 |

FOREIGN PATENT DOCUMENTS

| | | |
|---|---|---|
| DE | 202012000529 U1 | 2/2012 |
| DE | 10201409591 A1 | 11/2015 |
| EP | 2015721 | 1/2009 |
| EP | 2275062 A2 | 1/2011 |
| EP | 2698135 A1 | 2/2014 |
| JP | 04-257342 A | 9/1992 |
| JP | 2003190205 A | 7/2003 |
| WO | 9921520 A1 | 5/1999 |
| WO | 2013001312 A1 | 1/2013 |
| WO | 2014131976 A1 | 9/2014 |

OTHER PUBLICATIONS

First Indian Office Action from Indian Patent Application No. 201817023168 dated Oct. 22, 2020.
Japanese Notice of Reasons for Rejection dated Oct. 27, 2020 with Translation.

* cited by examiner

COMPRESSION DRESSING

This application claims priority to German Patent Application No. 10 2015 226 706.7 filed on Dec. 23, 2015.

The invention relates to a compression bandage comprising two layers.

In the prior art, compression bandages are, for example, used for diabetic ulcers. The problem here is that, owing to the symptoms, different issues must be taken into account, namely a sufficient compression, but also a cushioning action with respect to the limb to be treated.

One possibility is, for example, to apply a cushion and to apply a compression bandage thereover.

In this connection, a fundamental distinction has to be made in compression therapy between the so-called working pressure and the so-called resting pressure, where the resting pressure is the pressure which is exerted on the limb by the compression means, in this case the compression bandage, when the limb is horizontal. The working pressure is then the pressure which is exerted on the limb when the muscles are moving. Preferably, the working pressure ought to be 20 to 40 mm Hg above the resting pressure.

It is likewise known in this connection to use different bandage types. For instance, bandages that are known include so-called long-stretch bandages, which exhibit a very high elasticity and have in many cases a stretchability above 200%, and, by contrast, short-stretch bandages, which have only a low stretchability and only a low restoring force, but do not allow any further stretching at a very early point and are thus able to build up a comparatively high working pressure. By contrast, short-stretch bandages develop only a low resistance over a comparatively long range in order to then limit stretchability to a very great extent. Traditional short-stretch bandage compression therapy is a measure for treating venous disorders. In this case, the materials for short-stretch bandages are generally made from nonelastic materials and elastified by finishing processes. However, the elasticity decreases significantly during the treatment. This can lead to a reduction in the compression pressure during use.

Known compression bandages are, for example, described in EP 2 275 062 A2, which describes an internal skin-facing elastic bandage having a stretched elastic substrate and a stretched foam layer arranged on the skin-facing side of the substrate as well as a further stretched self-adhesive elastic bandage which is applied thereover.

Furthermore, DE 20 2012 000 529 U1 discloses a support, fastening or pressure bandage, the bandage here comprising at least four plies and having a tension ply which generates the restoring force and has holes, with the other plies being fixed to one another through the holes. Owing to the four intended plies, the bandage is comparatively expensive and complicated.

Furthermore, reference must be additionally made to WO 2014/131976 A2, which likewise relates to an elastic bandage, comprising a nonelastic layer which surrounds the elastic band and is connected thereto.

To achieve high therapeutic reliability, it is desirable that the therapeutically necessary compression pressure is achieved as easily as possible. To this end, a multiplicity of options are known in the prior art. For example, markers which deform at an excessively high stretch are known, making it possible for the therapist to identify an excessively high stretch and thus an excessively high application pressure. However, a disadvantage here is that this requires trained personnel at all times.

It is therefore desirable to provide a compression bandage which exhibits a high reliability of application and, at the same time, good therapeutic properties and which can in particular be worn for several days without determination of a distinct drop in the compression pressure.

Where the terms layer or ply are used, they refer to the same subject matter.

Proceeding from this prior art, the invention achieves the object by means of a compression bandage having the features of claim 1, wherein the two layers, namely the first cushioning layer and the second supporting layer, are connected to one another via an elastic thread by means of stitch-bonding methods and the stitch length is 1.5 to 3 mm/rotation at a sewing thread tension of no more than 4 cN.

What can be achieved by this design is that the two layers are connected by means of the stitch-bonding method and, in this case, preferably a Malimo or Maliwatt method, with the layers being connected in the unstretched state by means of the elastic sewing thread.

The advantage with a stitch-bonding method is that a connection can be simultaneously carried out at multiple points and the two layers can no longer be separated from one another after connection. Via the selection of the stitch length in the longitudinal direction of the fabric from which the compression bandages are then made up, where stitch length is to be understood to mean the distance between two stiches in the longitudinal stitching direction, and via the selection of the sewing thread tension, it is possible to adjust the stretchability of the elastic composite, resulting in an elastic composite which is composed of the two layers and which is no longer separable by hand and is nevertheless controllable. Depending on the selection of these parameters, the finished fabric contracts upon tension release and creases are thrown up in the material.

In this connection, the stitching technique and the stitch length of the sewing thread are regulated such that the fibers on the cushioning layer on the one side of the composite composed of the two layers exhibit skin comfort and equalization functions and, thus ultimately, the compression bandage has two discernibly different sides which are highly functional for pressure equalization. Furthermore, the stitch length must in this connection be adjusted such that the desired absorbent and skin-friendly properties of the skin-facing cushioning layer are maintained.

In this connection, the cushioning layer is the side of a compression bandage that faces a limb and the supporting layer is the second side applied thereon.

In this connection, use is made of the Malimo or Maliwatt method for connecting the layers, as known in the prior art. For example, the elasticity can be obtained by stitch-over of a rigid nonwoven or woven fabric with permanently elastic elastane threads in the longitudinal direction using the stitch-bonding technique MALIWATT or Malimo. The stitch-bonding technique MALIWATT or Malimo is described in *Malimo Nähwirktechnologie* [Malimo stitch-bonding technology], Ploch, Böttcher, Scharch, VEB Fachbuchverlag Leipzig, 1978, 1st edition.

Preferably, both layers, i.e., the cushioning layer and the supporting layer, can be nonelastic and are only elastified by means of the stitch-bonding method.

Particularly preferably, it can be envisaged that at least one of the two layers, but preferably both of the layers, composed of cushioning material and supporting layer are a nonwoven material. Alternatively, other materials such as, for example, woven fabrics, warp-knitted fabrics, weft-knitted fabrics or foams are, however, usable too. In this connection, the cushioning layer can be a wadding nonwoven layer, in particular a thermofusion nonwoven layer, which can optionally also already be preneedled. In this connection, in both methods, namely thermobonding and thermofusion, the fibers of the nonwovens are placed into a particular direction in a combing method and prepared as nonwoven rolls in a textile functionalization method and temperature-stabilized or temperature- and pressure-stabilized for further processing. During the thermofusion method, fibers with different melting points are fused together by means of hot-air dryers. In the thermobonding method, the fibers are fused between heated calender rolls by means of heat and pressure. In both cases, the result is soft, homogeneous nonwovens which are ideal and are suitable for technical applications. Owing to the lack of pressure, the thermofusion method is better suited to cushioning layers.

The supporting layer can be a thermobond nonwoven. In this case, the thermobond nonwoven preferably exhibits only a low stretchability and, at the same time, desired stiffness.

The two layers are fed together to a warp-knitting machine and connected to one another by means of an elastic sewing thread which can preferably be selected from a group composed of cotton spun crepe threads, cotton twisted crepe threads, textured polyamide yarns, textured polyester yarns, rubber threads or polyurethane elastane threads or a combination thereof.

The sewing thread can alternatively also be referred to as warp thread. In this case, the thread runs in the machine direction of the warp-knitting machine and not transversely thereto.

The compression-bandage fabric stitched to completion exhibits an optimized stretching at all times, and it can be particularly preferably envisaged that the maximum stretchability of the compression bandage, which corresponds to a predefined optimal stretchability, and a stretching of the compression bandage that goes beyond it is limited by a stretching threshold. This can significantly increase the reliability of application, since it is possible even for non-trained users to stretch the compression bandage maximally up to the stretching threshold, with not only the maximum stretchability, but simultaneously also the optimum stretching and thus the optimum compression pressure then being achieved, and to apply the compression bandage in this maximally stretched state.

To achieve an optimum cushioning action, it can be preferably envisaged that the thickness of the cushioning layer is 0.3-12 mm, preferably 0.4-6 mm and further preferably 0.5-3 mm, particularly preferably 0.6-1.2 mm.

Owing to the connection by means of a stitch-bonding method, the two layers in the tension-released state, after the stitched fabric has been further processed by means of make-up in the longitudinal direction to form the compression bandage, are set into waves such that an irregular surface of the compression bandage is formed. Owing to this irregular surface, what is also achieved, besides the primary function as equalization ply of the compression bandage and the secondary function of the regulatable stretchability and thus increased reliability of application, is that the waves give rise to a pattern on the surface, composed of protrusions in the material and indentations in the material, which is not completely suppressed even in the maximally stretched state, thereby additionally producing a massage or drainage effect during therapy.

To apply a resting pressure, it can be further envisaged to combine, in particular to overwrap, the compression bandage according to the invention with a further compression bandage, which can, for example, be in the form of a long-stretch bandage, i.e., to provide from the start of stretching a compression pressure which, however, does not rise abruptly.

As further bandage for the resting pressure, preference is given to using an elastic, cohesively adhesive nonwoven bandage of the type 752, brand name NOWOPRESS 752, manufacturer: Karl Otto Braun GmbH & Co. KG, Wolfstein, Germany, as compression bandage having long-stretch properties, wherein the base textile was obtained by stitch-over of a rigid polypropylene nonwoven with permanently elastic elastane threads in the longitudinal direction using the stitch-bonding technique MALIWATT. The stitch-bonding technique MALIWATT is described in *Malimo Nähwirktechnologie* [Malimo stitch-bonding technology], Ploch, Böttcher, Scharch, VEB Fachbuchverlag Leipzig, 1978, 1st edition. This bandage ply has been coated on both surfaces with a cohesively-adhesive adhesive based on polyisoprene rubber in order to achieve the desired cohesive adhesion effect. In this connection, the composition of the bandage ply LS (type 752) is as follows: 60% polypropylene, 12% elastane, 28% IR rubber Base nonwoven: PP spunbond nonwoven, 35 g/m$^2$, thermally embossed Sewing thread: 133 dtex elastane (DORLASTAN, BAYER)

Sewing thread density: 45 threads per 10 cm width

Sewing thread stitch length, stitching: 3 mm, open pillar stitch Areal weight, stretched: 59 g/m$^2$ Elasticity: In the longitudinal direction (warp direction)

Stretchability/retraction in accordance with DIN 61632: 160%/99%

Adhesive force, side A/B: 60 cN/cm.

The invention therefore also provides a combination bandage composed of the described bandage with cushioning layer and supporting layer and a further bandage which is, in particular, in the form of a long-stretch bandage for the resting pressure.

The division into the categories short-stretch, medium-stretch or long-stretch bandage is done according to stretchability and can, for example, be gathered from P. Asmussen, B. Söllner, *Kompressionstherapie Prinzipien and Praxis* [Compression therapy—principles and practice], Verlag Urban & Fischer in Elsevier, 2004, on page 121. The stretchabilities are determined in this case in accordance with DIN 61632.

The invention will be described in more detail below with reference to a drawing. Further advantages and features of the invention are additionally revealed by the rest of the application documents.

Figure 1:
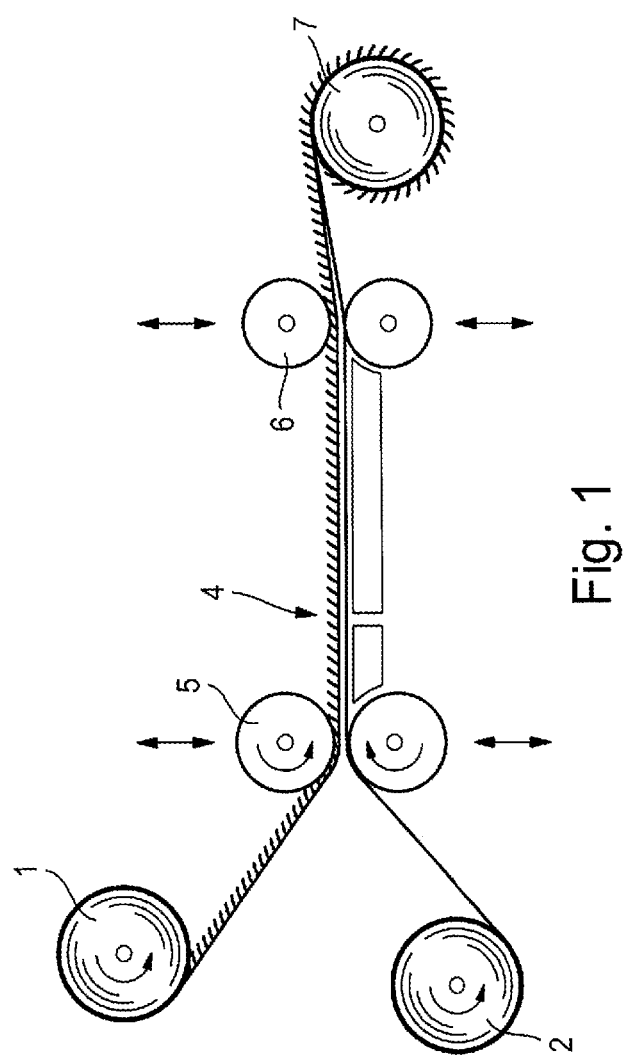
FIG. 1 shows a production method for such a compression bandage.

FIG. 1 depicts how a cushioning layer 1 composed of a wadding nonwoven and a supporting layer 2, here in the form of a thermobond nonwoven layer, are fed from a roll material and are connected to one another in a stitch-bonding method by means of a warp-knitting machine, identified by reference sign 4. In this process, the two plies are fixed to one another beforehand via a roller guide 5. The stitch-bonding method works here with a hook, by means of which the layers are overstitched with the elastic sewing threads. The material connected to one another via the elastic sewing thread is then guided through a further roller guide 6 and wound up on a roll 7, it being optionally possible beforehand to carry out make-up in the longitudinal direction to form bandages. The sewing thread is an elastically prestretched thread which is introduced with a predefined stitch length and a predefined sewing thread tension and thus leads to a contraction of the ply composite (fabric) after tension release of the elastic material.

Figure 2:
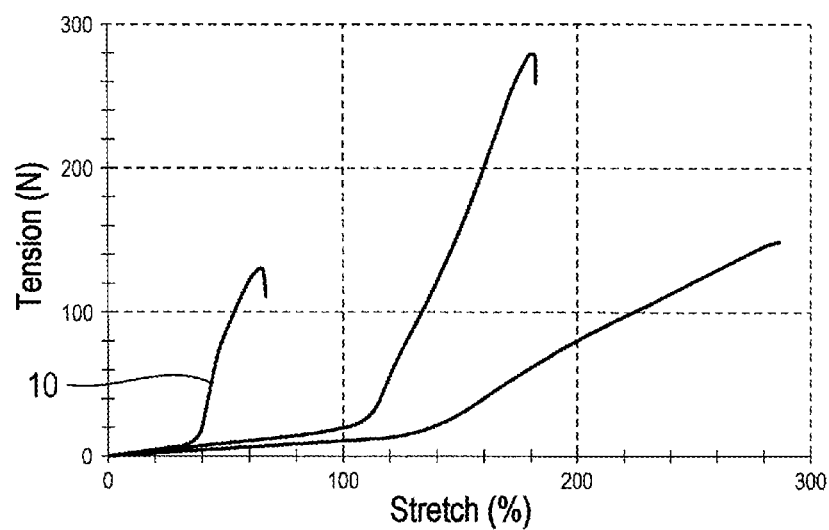
FIG. 2 shows a force/stretch graph for a finished compression bandage according to the invention.
Figure 3:
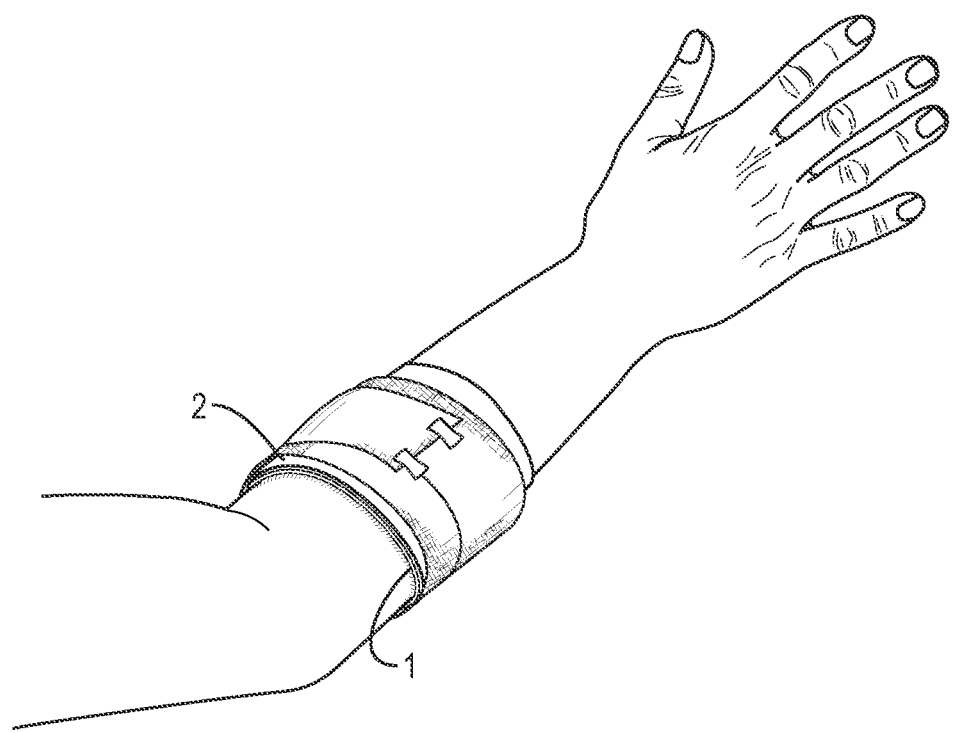
FIG. 3 shows a first cushioning layer and a second supporting layer of the compression bandage of the present invention.

FIG. 2 shows the force/stretch graph, where the compression bandage corresponds to the characteristics of a short-stretch bandage which initially exhibits approximately no increase in force upon stretching in order to then realize an abrupt rise and thus a stretching threshold, the stretching threshold here being in the range of the optimum therapeutic pressure, meaning that, upon maximum stretching of the compression bandage, it is simultaneously possible with application under this pretension to set the optimum therapeutic pressure for the compression therapy.

The stiffness of a bandage can be described by the elastic modulus and by the increase in force. FIG. 2 shows force/stretch graphs of the bandage 10 according to the invention (in comparison with two commercially available bandages). Here, the bandage according to the invention has a distinctly higher elastic modulus than the comparative bandages. The preferred values can be 4-10 N/mm$^2$, preferably 5-9 N/mm$^2$ and particularly preferably 6-8 N/mm$^2$.

The increase in force is the stretching the bandage has to carry out in order to be stretched from a significantly noticeable resistance of 20 N until ripping. It is possible to identify this behavior too from the graph according to FIG. 2. In the case of the bandage according to the invention, a force of approximately 20 N is achieved at a stretch of about 40%, and the bandage rips at a stretch of about 60%. In the range between 40 and 60% stretch, the bandage experiences a five- to ten-fold increase in force. In the case of the comparative products, a distinctly stronger stretch is required until ripping. Preferably, a bandage according to the invention (compression bandage) therefore has an increase in stretch of less than 50%, preferably less than 35%, particularly preferably less than 25%. The terms increase in force and increase in stretch describe synonymously the same issue.

The invention claimed is:

1. A compression bandage comprising a first cushioning layer (1) and a second supporting layer (2), wherein the first cushioning layer (1) and the second supporting layer (2) are connected to one another in an unstretched state via an elastic sewing thread by means of stitch-bonding where the stitch length is 1.5 to 3 mm at a sewing thread tension of not more than 4 cN, and wherein a material of the cushioning layer (1) and the supporting layer (2) is nonelastic and comprises a non-woven material; and wherein the compression bandage is only elasticized by means of stitch-bonding.

2. The compression bandage of claim 1, wherein a thickness of the cushioning layer (1) is 0.6-1.2 mm.

3. The compression bandage of claim 1, wherein the cushioning layer is comprised of a thermofusion nonwoven material.

4. The compression bandage of claim 1, wherein the supporting layer (2) is comprised of a thermobond nonwoven material.

5. The compression bandage of claim 1 wherein the elastic sewing thread is selected from the group consisting of cotton spun crepe threads, cotton twisted crepe threads, textured polyamide yarns, textured polyester yarns, rubber threads, polyurethane elastane threads and combinations thereof.

6. The compression bandage of claim 1, wherein the compression bandage has a stretching threshold which indicates a maximum stretchability.

7. The compression bandage of claim 6, wherein the maximum stretchability corresponds to a therapeutically predefined application of the compression bandage configured to be on a limb of a wearer.

8. The compression bandage of claim 1, wherein the compression bandage has an elastic modulus of 4-10 N/mm$^2$.

9. The compression bandage of claim 1, wherein the compression bandage has an increase in stretch of less than 50%.

10. A compression bandage combination comprising a first compression bandage as claimed in claim 1, and also a second compression bandage.

11. The compression bandage combination of claim 10, wherein the first compression bandage exerts a working pressure configured to be on a limb in an applied state and the second compression bandage a resting pressure.

12. The compression bandage of claim 8, wherein the compression bandage has an elastic modulus of 5-9 N/mm$^2$.

13. The compression bandage of claim 8, wherein the compression bandage has an elastic modulus of 6-8 N/mm$^2$.

14. The compression bandage of claim 9, wherein the compression bandage has an increase in stretch of less than 35%.

15. The compression bandage of claim 9, wherein the compression bandage has an increase in stretch of less than 25%.

16. The compression bandage combination of claim 10, wherein the second compression bandage is applicable over the first compression bandage.

17. The compression bandage of claim 1, wherein the first cushioning layer (1) is a wound contact layer.

18. A compression bandage consisting of a first cushioning layer (1) and a second supporting layer (2), wherein the first cushioning layer (1) and the second supporting layer (2) are connected to one another in the unstretched state via an elastic sewing thread by means of stitch-bonding where the stitch length is 1.5 to 3 mm at a sewing thread tension of not more than 4 cN, and wherein a material of the cushioning layer (1) and the supporting layer (2) is nonelastic and comprises a non-woven material; and wherein the compression bandage is only elasticized by means of stitch-bonding.

19. The compression bandage of claim 1, wherein the first cushioning layer (1) and the second supporting layer (2) are in direct contact with each other.

* * * * *